United States Patent
Amberden

(10) Patent No.: US 9,723,085 B1
(45) Date of Patent: Aug. 1, 2017

(54) TRANSFERRING A STATE OF USER INTERACTION WITH AN ONLINE CONTENT ITEM TO A COMPUTER PROGRAM

(71) Applicant: Google Inc., Mountain View, CA (US)

(72) Inventor: Aric Albert Beldon Amberden, Long Beach, CA (US)

(73) Assignee: Google, Inc., Mountain View, CA (US)

( * ) Notice: Subject to any disclaimer, the term of this patent is extended or adjusted under 35 U.S.C. 154(b) by 211 days.

(21) Appl. No.: 14/530,051

(22) Filed: Oct. 31, 2014

(51) Int. Cl.
  *G06F 15/16* (2006.01)
  *H04L 29/08* (2006.01)
  *H04L 12/24* (2006.01)
  *A63F 13/49* (2014.01)

(52) U.S. Cl.
  CPC ............ *H04L 67/142* (2013.01); *H04L 41/22* (2013.01); *A63F 13/49* (2014.09)

(58) Field of Classification Search
  USPC ......................................... 709/227, 228, 229
  See application file for complete search history.

(56) References Cited

U.S. PATENT DOCUMENTS

| | | | |
|---|---|---|---|
| 8,769,119 B2 | 7/2014 | Michaeli et al. | |
| 2011/0077086 A1* | 3/2011 | Grube | A63F 13/12 463/42 |
| 2012/0315993 A1* | 12/2012 | Dumont | G07F 17/3225 463/42 |
| 2013/0143669 A1* | 6/2013 | Muller | A63F 13/12 463/42 |
| 2013/0311285 A1 | 11/2013 | Abrol et al. | |
| 2014/0006374 A1 | 1/2014 | Forte et al. | |
| 2014/0164142 A1 | 6/2014 | Yang | |
| 2014/0274384 A1* | 9/2014 | Boswell | A63F 13/355 463/31 |

FOREIGN PATENT DOCUMENTS

WO 2014085681 A2 6/2014

\* cited by examiner

*Primary Examiner* — Joseph E Avellino
*Assistant Examiner* — Marshall McLeod
(74) *Attorney, Agent, or Firm* — Foley & Lardner LLP; John D. Lanza

(57) ABSTRACT

A computer-based method for transferring a state of user interaction with an online content item to a computer program accessible by a user device is provided. The method is implemented using an application server in communication with a memory. The method includes hosting a first session associated with a computer program. The first session includes a session state. The method also includes associating a first session token with the first session of the plurality of sessions, receiving from a user device one or more user interactions with an interactive online content item, updating the session state for the first session based on the one or more user interactions, receiving a request for the session state for the first session after the computer program becomes accessible for use by the user device, and transmitting the session state for the first session to be applied to the computer program.

18 Claims, 5 Drawing Sheets

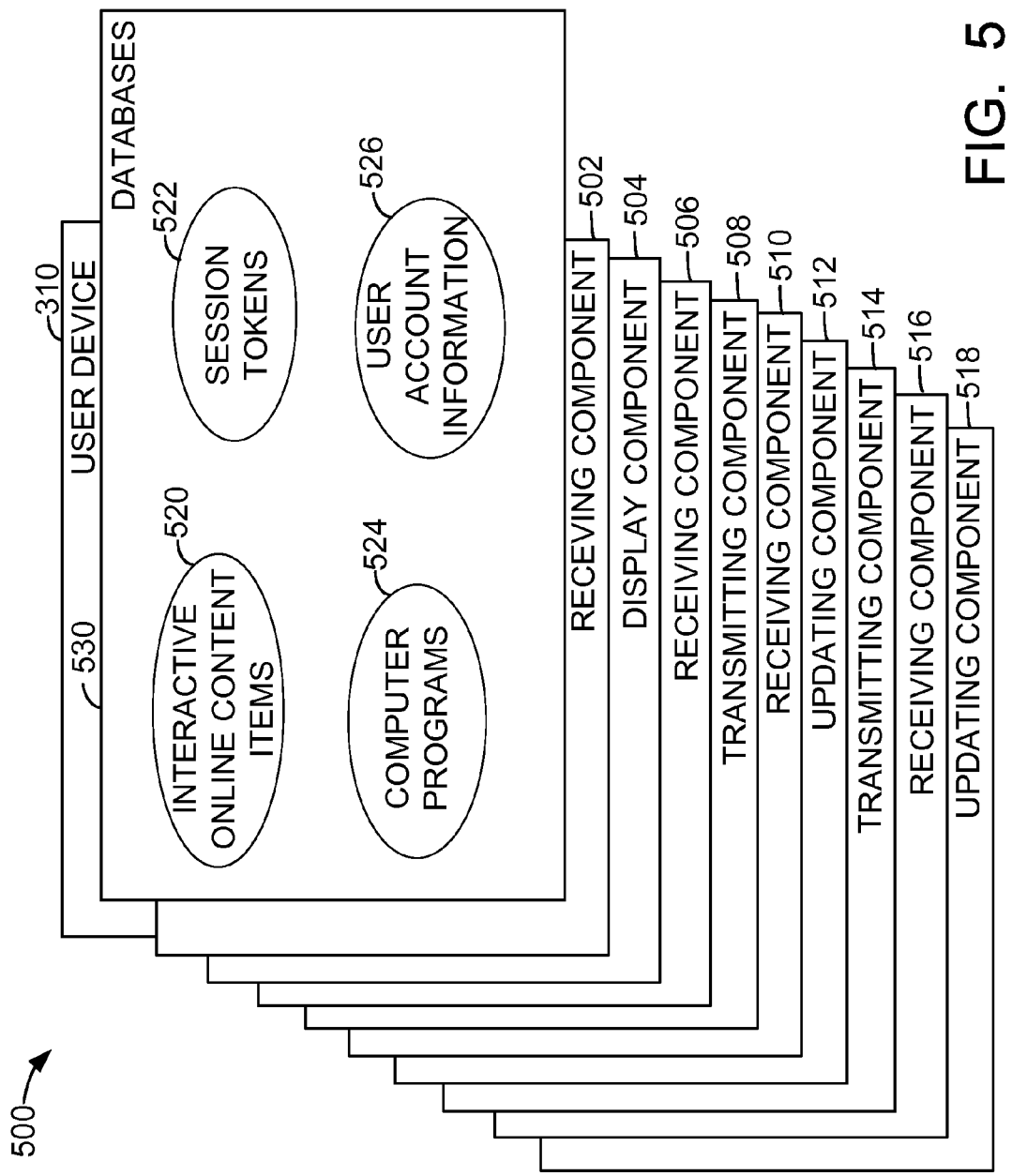

TRANSFERRING A STATE OF USER INTERACTION WITH AN ONLINE CONTENT ITEM TO A COMPUTER PROGRAM

BACKGROUND

This description relates to presenting online content items to a user that allow for user interaction, and more particularly to a network-based system and method for transferring a state of user interaction with an online content item to a computer program associated with the online content item, wherein the online content item is displayed on a user device and the computer program is accessible by the user device.

Internet users are able to view online publications (e.g., websites) on user devices. At least some of these online publications are displayed along with interactive online content items. At least some interactive online content items are advertisements that allow the user of the user device to interact directly with the advertisement. In some situations, the interactive online content item is advertising a computer program or computer application (otherwise known as an "app"), and the interactive online content item includes a simulation of the computer app. For example, the interactive online content item may be an advertisement for a computer game that allows the user to play the first few levels of the game. Once the user has interacted with the interactive online content item, the user may decide to acquire the computer program. The user may then visit an online store or other website where the user may acquire and install the computer program on their user device. In these known systems, the interactions between the user and the interactive online content item are lost when the user leaves the interactive online content item to acquire and install the computer program.

BRIEF DESCRIPTION OF THE DISCLOSURE

In one aspect, a computer-based method for transferring a state of user interaction with an online content item to a computer program accessible by a user device is provided. The method is implemented using an application server in communication with a memory. The method includes hosting on the application server a first session associated with a computer program. The first session includes a session state. The method also includes associating by the application server a first session token with the first session. The first session token uniquely identifies the first session. The method further includes receiving from a user device one or more user interactions with an interactive online content item. The interactive online content item is associated with the computer program. Moreover, the method includes updating the session state for the first session based on the one or more user interactions and receiving from the user device a request for the session state for the first session after the computer program becomes accessible for use by the user device. The request includes the first session token. Additionally, the method includes transmitting the session state for the first session to the user device to be applied to the computer program.

In another aspect, an application server for transferring a state of user interaction with an online content item to a computer program accessible by a user device is provided. The application server includes at least one processor communicatively coupled to at least one memory device. The application server is configured to host a first session associated with a computer program. The first session includes a session state. The application server is also configured to associate a first session token with the first session. The first session token uniquely identifies the first session. The application server is further configured to receive one or more user interactions with an interactive online content item from a user device. The interactive online content item is associated with the computer program. Moreover, the application server is further configured to update the session state for the first session based on the one or more user interactions and receive a request for the session state for the first session from the user device after the computer program becomes accessible for use by the user device. The request includes the first session token. Additionally, the application server is configured to transmit the session state for the first session to the user device to be applied to the computer program.

In yet another aspect, a computer-readable storage device having processor-executable instructions embodied thereon is provided. The processor-executable instructions are for transferring a state of user interaction with an online content item to a computer program accessible by a user device. When executed by an application server communicatively coupled to a memory, the processor-executable instructions cause the application server to host a first session associated with a computer program. The first session includes a session state. The processor-executable instructions also cause the application server to associate a first session token with the first session. The first session token uniquely identifies the first session. The processor-executable instructions further cause the application server to receive one or more user interactions with an interactive online content item from a user device. The interactive online content item is associated with the computer program. Moreover, the processor-executable instructions cause the application server to update the session state for the first session based on the one or more user interactions and receive a request for the session state for the first session from the user device after the computer program becomes accessible for use by the user device. The request includes the first session token. Additionally, the processor-executable instructions cause the application server to transmit the session state for the first session to the user device to be applied to the computer program.

In still another aspect, an online content management system for transferring a state of user interaction with an online content item to a computer program accessible by a user device is provided. The online content management system includes at least one processor communicatively coupled to at least one memory device. The online content management system includes a processor and a memory. The online content management server is in communication with a user device and an application server. The online content management system is configured to receive a session token for a session from the application server and transmit the session token and an interactive online content item to a user device. The interactive online content item is associated with a computer program, the session token uniquely identifies a session of the interactive online content item being hosted on an application server, and the user device is instructed to display the interactive online content item to the user. The online content management system is also configured to receive one or more user interactions with the interactive online content item and the session token from the user device and transmit the one or more user interactions and the session token to the application server. The application server updates a session state based on the one or more user interactions. The online content management system is further configured to receive user account information from the user device, associate the session token with the user account information, receive a user selection to acquire the computer program, and transmit the user account information and session token to the online store server. The online store server is configured to associated the session token with the computer program.

In another aspect, an application server for transferring a state of user interaction with an online content item to a computer program accessible by a user device is provided. The application server includes at least one processor communicatively coupled to at least one memory device. The application server includes a means for hosting on the application server a first session associated with a computer program. The first session includes a session state. The application server also includes a means for associating by the application server a first session token with the first session. The first session token uniquely identifies the first session. The application server further includes a means for receiving from a user device one or more user interactions with an interactive online content item. The interactive online content item being associated with the computer program. Moreover, the application server includes a means for updating the session state for the first session based on the one or more user interactions. In addition the application server includes a means for receiving from the user device a request for the session state for the first session after the computer program becomes accessible for use by the user device. The request includes the first session token. Additionally, application server includes a means for transmitting the session state for the first session to the user device to be applied to the computer program.

In another aspect, an application server as described above is provided, additionally including a means for generating the first session token. The application server also includes a means for transmitting to an online content management system the first session token and the interactive online content item. The interactive online content item is to be displayed on the user device and allow the user to interact with the acquirable computer program.

In another aspect, an application server as described above is provided, additionally including a means for hosting a plurality of sessions associated with the computer program. The application server also includes a means for receiving the first session token. The application server further includes a means for determining a first session from the plurality of sessions without an associated session token. Moreover, the application server further a means for associating the first session token with the first session.

In another aspect, an application server as described above is provided, additionally including a means for determining one or more responses to the one or more user interactions. The one or more responses are generated from inputting the one or more user interactions into the computer program. The application server also includes a means for transmitting to the user device the one or more responses for display on the user device within the interactive online content item. The application server further includes a means for updating the session state based on the one or more responses.

In another aspect, an application server as described above is provided, additionally including a means for hosting a plurality of sessions associated with the computer program, wherein each session of the plurality of sessions includes a simulation of the computer program being executed.

In another aspect, an application server as described above is provided, wherein the first session is configured to enable the user device to interact with the computer program through the interactive online content item.

In another aspect, an application server as described above is provided, additionally including a means for hosting the computer program. The computer program is accessible via a user account. The application server also includes a means for receiving user account information to access the user account. The application server further includes a means for transmitting to an online store server a request for session tokens. The request includes the user account information. Moreover, the application server includes a means for receiving from the online store server one or more session tokens associated with the user account information. In addition, the application server also includes a means for retrieving the session state for each session associated with each of the one or more session tokens. Additionally, the application server also includes a means for updating at least one attribute of the user account based on at least one of the retrieved session states.

In another aspect, an application server as described above is provided, wherein the request for the session state for the first session is received from an online store server, and the session state for the first session is transmitted to the online store server to be included with the computer program when the user device downloads the computer program.

In another aspect, an application server as described above is provided, wherein the interactive online content item includes a link to acquire the computer program, and wherein the link directs the user device to an online store server where the user may acquire the computer program.

BRIEF DESCRIPTION OF THE DRAWINGS

FIG. 5 is a diagram of a plurality of components of one or more example computing devices, included in the environment shown in FIG. 1.

Figure 1:
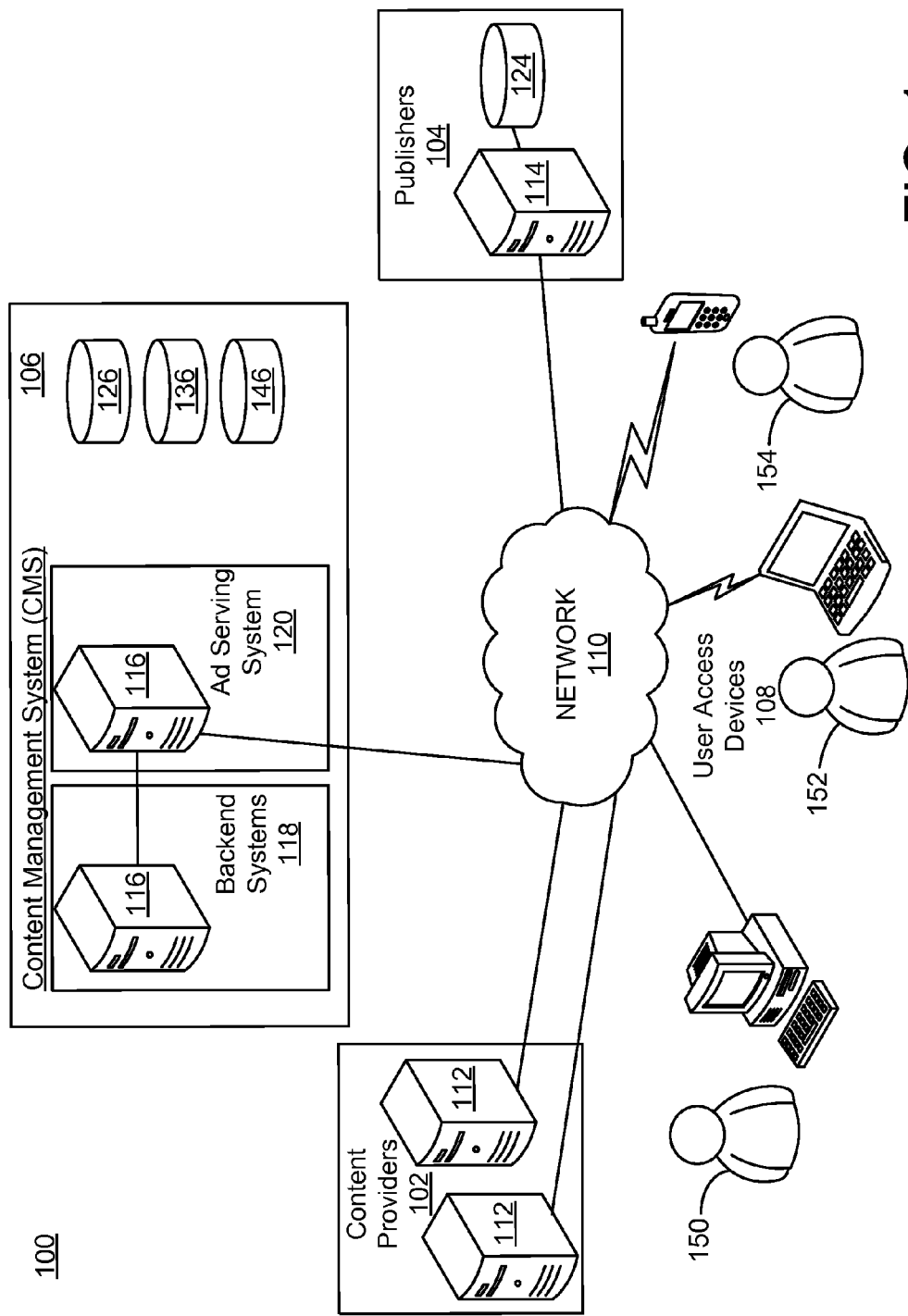
FIG. 1 is a diagram depicting an example networked environment for transferring a state of user interaction with an online content item to a computer program associated with the online content item and accessible by a user computer device.

Although specific features of various embodiments may be shown in some drawings and not in others, this is for convenience only. Any feature of any drawing may be referenced and/or claimed in combination with any feature of any other drawing.

DETAILED DESCRIPTION OF THE DISCLOSURE

The following detailed description of implementations refers to the accompanying drawings. The same reference numbers in different drawings may identify the same or similar elements. Also, the following detailed description does not limit the claims.

The subject matter described herein relates to linking a state of a user interaction with an online content item (e.g., an online advertisement) to a computer program (e.g., a computer app) that is associated with the online content item, and accessible by or installed on the user computer device. As described herein, an interactive online content item is associated with a provider of a computer program. The interactive online content item is configured to: (i) display on a user device, (ii) enable a user to interact with an interactive session of at least a simulation of the computer program, and (iii) direct the user to a web page to acquire the computer program if the user so desires.

In addition, the interactive online content item includes a session token. The session token uniquely identifies the interactive session of the computer program embedded within the interactive online content item. In some embodiments, the interactive online content item executes a full version or a limited version of the computer program for the user to interact with. In other embodiments, the interactive online content item executes a simulation of the computer program, with potentially reduced functionality. The interactive session (i.e., the interactions of the user with the computer program embedded within the online content item) is hosted on an application server (i.e., the server hosting computer program that the user device is interacting with) which stores the state of the interactions between the user and the interactive online content item. When the user acquires the computer program, the session token is passed to the computer program to identify the interactive session. In the example embodiment, the computer program uses the session token to retrieve from the application server the state of user interaction (also known as session state) between the user and the interactive online content item. In the example embodiment, the computer program uses the state of user interaction to update at least one attribute of the computer program.

In the example embodiment, an online content management server (OCMS) causes an interactive online content item to be displayed on a user device. The OCMS causes a session identifier to be provided to the user device to be associated with the interactive online content item. The user interacts with the computer program hosted on the application server through the interactive online content item. The user decides to install the computer program on the user device from a store server. The OCMS transmits the session identifier to the store server. The computer program is transferred to the user device from the store server. The computer program includes the session token. The computer program provides the session identifier to the application server. The application server provides session information about the session associated with the session identifier. The computer program on the user device is updated based on the session information.

In the example embodiment, OCMS (e.g., Double-click for Publisher) serves an interactive online content item (e.g., interactive advertisement) to a user device. In the example embodiment, the interactive online content item is an advertisement for a computer program or application (e.g., a game or messaging app) that allows the user of the user device to interact directly with the advertisement. In some embodiments, the interactive online content item is a simulation of the computer program, in other embodiments the interactive online content item is the actual computer program. For example, the interactive online content item may be an advertisement for a game and allow the user to play the first couple levels of the game. In other examples, the interactive online content item may be for a messaging program or a grocery list generator that allow the user to try the program.

In the example embodiment, the interactive online content item includes a link to an interactive session of the computer program, which is hosted on an application server. In the example embodiment, the application server hosts a plurality of instances of the computer program, and stores the user interactions with each instance of the computer program. In some embodiments, the application server is associated with the creator of the computer program (i.e., the developer). In other embodiments, the application server is associated with the advertiser of the computer program (i.e., the advertising or marketing company). In still other embodiments, the application server is associated with the seller of the computer program (i.e., the computer game store).

When the OCMS serves the interactive online content item to the user device, the OCMS also includes a session token with the online content item to identify which interactive session is connected to that interactive online content item. In the example embodiment, the interactive online content item directly communicates with the application server. For example, every interaction that the user makes is transmitted from the user device to the session on the application server associated with that interactive online content item. The application server hosts the computer program, stores the interactions received from the user, and determines the response that the computer program makes. The application server transmits the response back to be displayed on the user device. In other embodiments, the interactive online content item is in indirect communication with the application server. For example, the interactive online content item simulates the computer program by receiving user interactions and displaying responses. At periodic intervals (i.e., when a level of the game is completed), the interactive online content item transmits the current state of user interaction (i.e., score, level, and bonuses earned) and the session token from the user device to the application server. The application server stores the current state of user interaction and associates it with the session token.

In some other embodiments, the interactive online content item communicates with the application server through the OCMS. These communications include the session token to identify which session on the application server the communications are associated with. In some embodiments, the OCMS is aware of the user's account information (i.e., the user is logged in while interacting with the interactive online content item). In these embodiments, the OCMS associates the user's identity with the session token. The user of the user device then interacts with the interactive online content item, for example playing the first two levels of the game. The application server stores the state of interaction between the interactive online content item and the user. In the game example, the state of interaction could include the score, level, and any bonuses or awards that the user has earned. For the messaging program, the state of interaction may include any messages sent, messages received, and any contacts in the program.

When the user decides to acquire or install the computer program on the user device, the interactive online content item provides a virtual button or other selectable object to direct the user to a portion of an online store hosted on an online store server, where the user may acquire or download the computer program. The online store could also be an application store on a mobile device, a website, or other online location to acquire the computer program. In the example embodiment, the OCMS transmits the session token to the online store server, which the online store server associates with the computer program. In other embodiments, the OCMS may transfer the session token and the user identity to online store server. In some embodiments, the user provides an identity to the online store server, which associates that identity with the session token.

In some embodiments, the online store server embeds the user token in the computer program. After the user downloads or accesses the computer program, the computer program communicates the session token to the application server to retrieve the state of user interaction. In other embodiments, the online store server communicates the session token directly to the application server via an application programming interface (API) and receives the state of user interaction. In yet another embodiment, the online store server may provide an API, which allows the application server to transmit a user identity to the online store server. The online store server responds with all session tokens related to that user identity for all computer programs that the application server is responsible for. The API would also indicate which computer program is associated with each session token.

Once the user has acquired the computer program from the online store server, the computer program uses the session token to retrieve the state of interaction from the application server. The computer program then changes at least one attribute based on the state of interaction. For example, if the user had completed the first two levels of a game, then the computer program would allow the user to keep his or her score from the interactive online content item and play the third level of the game. In another example, if the program was a messaging program, then the computer program would be updated with any messages that the user had sent or received while using the interactive online content item.

In some embodiment, the user acquires an account for the computer program, where the computer program is executed on an application server. The online store server associates the session token with the account for the computer program. Upon activation of the account, the application server uses the session token to access the state of user interaction and updates the account based on the state of user interaction.

In some embodiments, the user may actually already own the computer program and by interacting with the interactive online content item and then opening the computer program, the user might earn a bonus for returning to the computer program. In these embodiments, the session token is transmitted directly or indirectly to the computer program.

As used herein, an element or step recited in the singular and proceeded with the word "a" or "an" should be understood as not excluding plural elements or steps, unless such exclusion is explicitly recited. Furthermore, references to "one embodiment" of the subject matter disclosed herein are not intended to be interpreted as excluding the existence of additional embodiments that also incorporate the recited features.

The methods and systems described herein may be implemented using computer programming or engineering techniques including computer software, firmware, hardware, or any combination or subset. As disclosed above, at least one technical problem with known systems is that any interactions that a user may have with an interactive online content item are lost when the user leaves the interactive online content item to purchase the computer program associated with that interactive online content item. The systems and methods described herein address that technical problem. The technical effect of the systems and processes described herein is achieved by performing at least one of the following steps: (a) receiving, from an online content management server, an interactive online content item and a session token, wherein the interactive online content item is associated with a computer program, wherein the interactive online content item includes a link to acquire the computer program, and wherein the session token identifies a session of the interactive online content item being hosted on an application server; (b) displaying, to the user, the interactive online content item; (c) receiving, from the user, one or more user interactions with the interactive online content item; (d) transmitting, to the application server, the one or more user interactions, wherein the application server generates one or more updates to the interactive online content item based on the one or more user interactions; (e) receiving, from the application server, the one or more updates to the interactive online content item; (f) updating the interactive online content item based on the one or more updates; (g) displaying, to the user, the updated interactive content item; (h) transmitting, to the application server, the one or more user interactions, wherein the application server updates a session state based on the one or more user interactions; (i) receiving a user selection to acquire the computer program; transmitting the user selection to an online store server where the user may acquire the computer program; (j) transmitting user account information to the online content management server wherein the online content management server associates the session token with the user account information; (k) instructing the online content management server to transmit the user account information and session token to the online store server; (l) receiving the computer program from the online store server, wherein the received computer program includes the session token; retrieving the session token from the computer program; (m) transmitting the session token to the application server to request the session state; (n) receiving, from the application server, the session state based on the session token; and (o) updating, by the client computing device, at least one attribute of the computer program based on the session state. The resulting technical effect is that user interactions with an interactive online content item may be linked to the associated computer program and used to update that computer program after the user has acquired the computer program. By linking, the system is made more efficient because the interactions with the computer program through the interactive online content item are saved and applied to the computer program so that users do not have to repeat those actions after acquiring the computer program.

FIG. 1 is a diagram depicting an example networked environment for transferring a state of user interaction with an online content item to a computer program associated with the online content item and accessible by a user computer device. With reference to FIG. 1, an example networked environment 100 may include one or more content providers 102, one or more publishers 104, a content management system (CMS) 106, and one or more user access devices 108 ("client computing devices" or "user devices"), which may be coupled to a network 110. User access devices are used by users 150, 152, and 154. Each of the elements 102, 104, 106, 108 and 110 in FIG. 2 may be implemented or associated with hardware components, software components, or firmware components or any combination of such components. The elements 102, 104, 106, 108 and 110 can, for example, be implemented or associated with general purpose servers, software processes and engines, and/or various embedded systems. The elements 102, 104, 106 and 110 may serve, for example, as a content distribution network. In the example embodiment, content providers 102 include advertisers, and CMS 106 is an advertising management system.

The content providers 102 may include any entities that are associated with content (i.e., a content item or multiple content items). In some embodiments, the content includes any form of communication in which one or more products, services, ideas, messages, people, organizations or other items are identified and promoted (or otherwise communicated). Content is not limited to advertisements and commercial promotions. Rather, content may include public service announcements or any other types of notices, such as public notices published in printed or electronic press or broadcasts.

Content may be communicated via various mediums and in various forms. In some examples, content may be communicated through an interactive medium, such as the Internet, and may include graphical content (e.g., banner content), textual content, image content, audio content, video content, content combining one of more of any of such components, or any form of electronically delivered content. Content may include embedded information, such as embedded media, links, meta-information, and/or machine executable instructions. Content could also be communicated through RSS (Really Simple Syndication) feeds, radio channels, television channels, print media, and other media.

Content can refer to both a single "creative" and a "content group." A creative refers to any entity that represents one content impression. A content impression refers to any form of presentation of content such that it is viewable/receivable by a user. In some examples, a content impression may occur when content is displayed on a display device of a user access device (i.e., a "client computing device" or "user device"). A content group refers, for example, to an entity that represents a group of creatives that share a common characteristic, such as having the same content selection and recommendation criteria. Content groups can be used to create a content campaign.

The content providers 102 may provide (or be otherwise associated with) products and/or services related to content. The content providers 102 may include or be associated with, for example, retailers, wholesalers, warehouses, manufacturers, distributors, health care providers, educational establishments, financial establishments, technology providers, energy providers, utility providers, or any other product or service providers or distributors.

The content providers 102 may directly or indirectly generate, maintain, and/or analyze content, which may be related to products or services offered by or otherwise associated with the content providers 102. The content providers 102 may include or maintain one or more data processing systems 112, such as servers or embedded systems, coupled to the network 110. The content providers 102 may include or maintain one or more processes that run on one or more data processing systems.

The publishers 104 may include any entities that generate, maintain, provide, present and/or otherwise process publications in the environment 100. "Publishers," in particular, include authors of publications, wherein authors may be individual persons, or, in the case of works made for hire, the proprietor(s) who hired the individual(s) responsible for creating the online publications. The term "publication" refers to various types of web-based, software application-based and/or otherwise presented information, including articles, discussion threads, reports, analyses, financial statements, music, video, graphics, search results, web page listings, information feeds (e.g., RSS feeds), television broadcasts, radio broadcasts, printed information, or any other form of information that may be presented to a user using a computing device such as one of user access devices 108.

In some implementations, the publishers 104 may include publishers with an Internet presence, such as online publication and news providers (e.g., online newspapers, online magazines, television websites, etc.), online service providers (e.g., financial service providers, health service providers, etc.), and the like. The publishers 104 can include software application providers, television broadcasters, radio broadcasters, satellite broadcasters, and other providers of publications. One or more of the publishers 104 may represent a publication network that is associated with the CMS 106.

The publishers 104 may receive requests from the user access devices 108 (or other elements in the environment 100) and provide or present publications to the requesting devices. The publishers may provide or present publications via various mediums and in various forms, including web based and non-web based mediums and forms. The publishers 104 may generate and/or maintain such publications and/or retrieve the publications from other network resources.

In addition to publications, the publishers 104 may be configured to integrate or combine retrieved publications with content that is related or relevant to the retrieved publication for display to users 150, 152, and 154. The relevant content may be provided from the CMS 106 and may be combined with a publication for display to users 150, 152, and 154. In some examples, the publishers 104 may retrieve a publication for display on a particular user access device 108 and then forward the publication to the user access device 108 along with code that causes content from the CMS 106 to be displayed to the user 150, 152, or 154. In other examples, the publishers 104 may retrieve a publication, retrieve relevant content (e.g., from the CMS 106 or the content providers 102), and then integrate the content and the publication to form a page for display to the user 150, 152, or 154.

As noted above, one or more of the publishers 104 may represent a publication network. In such an implementation, the content providers 102 may be able to present content to users through this publication network.

The publishers 104 may include or maintain one or more data processing systems 114, such as servers or embedded systems, coupled to the network 110. They may include or maintain one or more processes that run on data processing systems. In some examples, the publishers 104 may include one or more publication repositories 124 for storing publications and other information.

The CMS 106 manages content and provides various services to the content providers 102, the publishers 104, and the user access devices 108. The CMS 106 may store content in a content repository 126 and facilitate the distribution or selective provision and recommendation of content through the environment 100 to the user access devices 108.

The CMS 106 may include one or more data processing systems 116, such as servers or embedded systems, coupled to the network 110. It can also include one or more processes, such as server processes. In some examples, the CMS 106 may include a content serving system 120 and one or more backend processing systems 118. The content serving system 120 may include one or more data processing systems 116 and may perform functionality associated with delivering content to publishers or user access devices 108. The backend processing systems 118 may include one or more data processing systems 116 and may perform functionality associated with identifying relevant content to deliver, processing various rules, performing filtering processes, generating reports, maintaining accounts and usage information, and other backend system processing. The CMS 106 can use the backend processing systems 118 and the content serving system 120 to selectively recommend and provide relevant content from the content providers 102 through the publishers 104 to the user access devices 108.

The CMS 106 may include or access one or more crawling, indexing and searching modules (not shown). These modules may browse accessible resources (e.g., the World Wide Web, publisher content, data feeds, etc.) to identify, index and store information. The modules may browse information and create copies of the browsed information for subsequent processing. The modules may also check links, validate code, harvest information, and/or perform other maintenance or other tasks.

Searching modules may search information from various resources, such as the World Wide Web, publications, intranets, newsgroups, databases, and/or directories. The search modules may employ one or more known search or other processes to search data. In some implementations, the search modules may index crawled content and/or content received from data feeds to build one or more search indices. The search indices may be used to facilitate rapid retrieval of information relevant to a search query.

The CMS 106 may include one or more interface or frontend modules for providing the various features to content providers, publishers, and user access devices. For example, the CMS 106 may provide one or more publisher front-end interfaces (PFEs) for allowing publishers to interact with the CMS 106. The CMS 106 may also provide one or more content provider front-end interfaces (CPFEs) for allowing content providers to interact with the CMS 106. In some examples, the front-end interfaces may be configured as web applications that provide users with network access to features available in the CMS 106.

The CMS 106 provides various content management features to the content providers 102. The CMS 106 features may allow users to set up user accounts, set account preferences, create content, select keywords for content, create campaigns or initiatives for multiple products or businesses, view reports associated with accounts, analyze costs and return on investment, selectively identify customers in different regions, selectively recommend and provide content to particular publishers, analyze financial information, analyze content performance, estimate content traffic, access keyword tools, add graphics and animations to content, etc.

The CMS 106 may allow the content providers 102 to create content and input keywords for which the content will appear. In some examples, the CMS 106 may provide content to user access devices or publishers when keywords associated with that content are included in a user request or a requested publication. The CMS 106 may also allow the content providers 102 to set bids for content. A bid may represent the maximum amount a content provider is willing to pay for each content impression, user click-through of content or other interaction with content. A click-through can include any action a user takes to select content. The content providers 102 may also choose a currency and monthly budget.

The CMS 106 may also allow the content providers 102 to view information about content impressions, which may be maintained by the CMS 106. The CMS 106 may be configured to determine and maintain the number of content impressions relative to a particular website or keyword. The CMS 106 may also determine and maintain the number of click-throughs for content as well as the ratio of click-throughs to impressions.

The CMS 106 may also allow the content providers 102 to select and/or create conversion types for content. A "conversion" may occur when a user consummates a transaction related to given content. A conversion could be defined to occur when a user clicks on content, for example a specific content item, is referred to the content provider's web page, and consummates a purchase there before leaving that web page. In another example, a conversion could be defined as the display of content to a user and a corresponding purchase on the content provider's web page within a predetermined time (e.g., seven days). The CMS 106 may store conversion data and other information in a conversion data repository 136.

The CMS 106 may allow the content providers 102 to input description information associated with content. This information could be used to assist the publishers 104 in determining content to publish. The content providers 102 may additionally input a cost/value associated with selected conversion types, such as a five dollar credit to the publishers 104 for each product or service purchased.

The CMS 106 may provide various features to the publishers 104. The CMS 106 may deliver content (associated with the content providers 102) to the user access devices 108 when users access publications from the publishers 104. The CMS 106 can be configured to deliver content that is relevant to publisher sites, publications, and publisher audiences.

In some examples, the CMS 106 may crawl publications provided by the publishers 104 and deliver content that is relevant to publisher sites, publications and publisher audiences based on the crawled publications. The CMS 106 may also selectively recommend and/or provide content based on user information and behavior, such as particular search queries performed on a search engine website. The CMS 106 may store such information in a general database 146. In some examples, the CMS 106 can add search to a publisher site and deliver content configured 102 to provide appropriate and relevant content relative to search results generated by requests from visitors of the publisher site. A combination of these and other approaches can be used to deliver relevant content.

The CMS 106 may allow the publishers 104 to search and select specific products and services as well as associated content to be displayed with publications provided by the publishers 104. For example, the publishers 104 may search through content in the content repository 126 and select certain content for display with their publications.

The CMS 106 may be configured to selectively recommend and provide content created by the content providers 102 to the user access devices 108 directly or through the publishers 104. The CMS 106 may selectively recommend and provide content to a particular publisher 104 (as described in further detail herein) or a requesting user access device 108 when a user requests search results or loads a publication from the publisher 104.

In some implementations, the CMS 106 may manage and process financial transactions among and between elements in the environment 100. For example, the CMS 106 may credit accounts associated with the publishers 104 and debit accounts of the content providers 102. These and other transactions may be based on conversion data, impressions information and/or click-through rates received and maintained by the CMS 106.

"Computing devices", for example user access devices 108, may include any devices capable of receiving information from the network 110. The user access devices 108 could include general computing components and/or embedded systems optimized with specific components for performing specific tasks. Examples of user access devices include personal computers (e.g., desktop computers), mobile computing devices, cell phones, smart phones, head-mounted computing devices, media players/recorders, music players, game consoles, media centers, media players, electronic tablets, personal digital assistants (PDAs), television systems, audio systems, radio systems, removable storage devices, navigation systems, set top boxes, other electronic devices and the like. The user access devices 108 can also include various other elements, such as processes running on various machines.

The network 110 may include any element or system that facilitates communications among and between various network nodes, such as elements 108, 112, 114 and 116. The network 110 may include one or more telecommunications networks, such as computer networks, telephone or other communications networks, the Internet, etc. The network 110 may include a shared, public, or private data network encompassing a wide area (e.g., WAN) or local area (e.g., LAN). In some implementations, the network 110 may facilitate data exchange by way of packet switching using the Internet Protocol (IP). The network 110 may facilitate wired and/or wireless connectivity and communication.

For purposes of explanation only, certain aspects of this disclosure are described with reference to the discrete elements illustrated in FIG. 2. The number, identity and arrangement of elements in the environment 100 are not limited to what is shown. For example, the environment 100 can include any number of geographically-dispersed content providers 102, publishers 104 and/or user access devices 108, which may be discrete, integrated modules or distributed systems. Similarly, the environment 100 is not limited to a single CMS 106 and may include any number of integrated or distributed CMS systems or elements.

Figure 2:
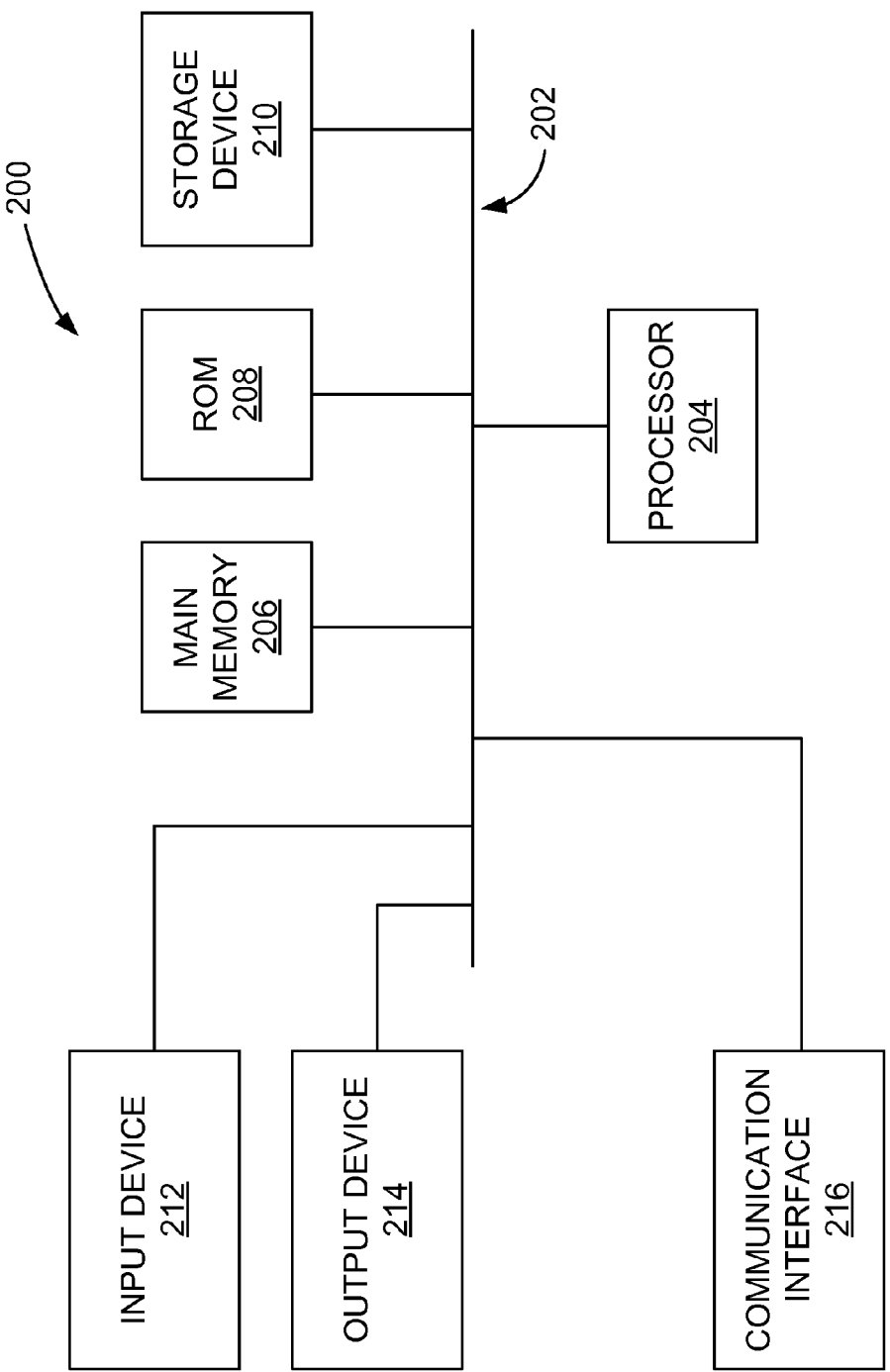
FIG. 2 is a block diagram of an example computing device used for transferring a state of user interaction with an online content item to a computer program associated with the online content item and accessible by a user computer device, as shown in the environment of FIG. 1.

Furthermore, additional and/or different elements not shown may be contained in or coupled to the elements shown in FIG. 2, and/or certain illustrated elements may be absent. In some examples, the functions provided by the illustrated elements could be performed by less than the illustrated number of components or even by a single element. The illustrated elements could be implemented as individual processes running on separate machines or a single process running on a single machine.

FIG. 2 is a block diagram of an example computing device 200 used for transferring a state of user interaction with an online content item to a computer program associated with the online content item and accessible by a user computer device, as shown in the environment of FIG. 1. More specifically, computing device 200 is configured to transmit online content requests to multiple content providers simultaneously or nearly simultaneously. Computing device 200 is intended to represent various forms of digital computers, such as laptops, desktops, workstations, personal digital assistants, servers, blade servers, mainframes, and other appropriate computers. Computing device 200 is also intended to represent various forms of mobile devices, such as personal digital assistants, cellular telephones, smart phones, phablets, and other similar computing devices. The components shown here, their connections and relationships, and their functions, are meant to be examples only, and are not meant to limit implementations of the subject matter described and/or claimed in this document.

In the example embodiment, computing device 200 could be user access device 108 or any of data processing systems 112, 114, or 116 (shown in FIG. 1). Computing device 200 may include a bus 202, a processor 204, a main memory 206, a read only memory (ROM) 208, a storage device 210, an input device 212, an output device 214 (also known as a display), and a communication interface 216. Bus 202 may include a path that permits communication among the components of computing device 200.

Processor 204 may include any type of conventional processor, microprocessor, or processing logic that interprets and executes instructions. Processor 204 can process instructions for execution within the computing device 200, including instructions stored in the memory 206 or on the storage device 210 to display graphical information for a GUI on an external input/output device, such as display 214 coupled to a high speed interface. In other implementations, multiple processors and/or multiple buses may be used, as appropriate, along with multiple memories and types of memory. Also, multiple computing devices 200 may be connected, with each device providing portions of the necessary operations (e.g., as a server bank, a group of blade servers, or a multi-processor system).

Main memory 206 may include a random access memory (RAM) or another type of dynamic storage device that stores information and instructions for execution by processor 204. ROM 208 may include a conventional ROM device or another type of static storage device that stores static information and instructions for use by processor 204. Main memory 206 stores information within the computing device 200. In one implementation, main memory 206 is a volatile memory unit or units. In another implementation, main memory 206 is a non-volatile memory unit or units. Main memory 206 may also be another form of computer-readable medium, such as a magnetic or optical disk.

Storage device 210 may include a magnetic and/or optical recording medium and its corresponding drive. The storage device 210 is capable of providing mass storage for the computing device 200. In one implementation, the storage device 210 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as main memory 206, ROM 208, the storage device 210, or memory on processor 204.

The high speed controller manages bandwidth-intensive operations for the computing device 200, while the low speed controller manages lower bandwidth-intensive operations. Such allocation of functions is for purposes of example only. In one implementation, the high-speed controller is coupled to main memory 206, display 214 (e.g., through a graphics processor or accelerator), and to high-speed expansion ports, which may accept various expansion cards (not shown). In the implementation, low-speed controller is coupled to storage device 210 and low-speed expansion port. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

Input device 212 may include a conventional mechanism that permits computing device 200 to receive commands, instructions, or other inputs from a user 150, 152, or 154, including visual, audio, touch, button presses, stylus taps, etc. Additionally, input device may receive location information. Accordingly, input device 212 may include, for example, a camera, a microphone, one or more buttons, a touch screen, and/or a GPS receiver. Output device 214 may include a conventional mechanism that outputs information to the user, including a display (including a touch screen) and/or a speaker. Communication interface 216 may include any transceiver-like mechanism that enables computing device 200 to communicate with other devices and/or systems. For example, communication interface 216 may include mechanisms for communicating with another device or system via a network, such as network 110 (shown in FIG. 1).

As described herein, computing device 200 facilitates the presentation of content from one or more publishers, along with one or more sets of sponsored content, for example ads, to a user. Computing device 200 may perform these and other operations in response to processor 204 executing software instructions contained in a computer-readable medium, such as memory 206. A computer-readable medium may be defined as a physical or logical memory device and/or carrier wave. The software instructions may be read into memory 206 from another computer-readable medium, such as data storage device 210, or from another device via communication interface 216. The software instructions contained in memory 206 may cause processor 204 to perform processes described herein. Alternatively, hardwired circuitry may be used in place of or in combination with software instructions to implement processes consistent with the subject matter herein. Thus, implementations consistent with the principles of the subject matter disclosed herein are not limited to any specific combination of hardware circuitry and software.

The computing device 200 may be implemented in a number of different forms, as shown in the figure. For example, it may be implemented as a standard server, or multiple times in a group of such servers. It may also be implemented as part of a rack server system. In addition, it may be implemented in a personal computer such as a laptop computer. Each of such devices may contain one or more of computing device 200 and an entire system may be made up of multiple computing devices 200 communicating with each other.

The processor 204 can execute instructions within the computing device 200, including instructions stored in the main memory 206. The processor may be implemented as chips that include separate and multiple analog and digital processors. The processor may provide, for example, for coordination of the other components of computing device 200, such as control of user interfaces, applications run by computing device 200, and wireless communication by computing device 200. Instructions may be stored by a cloud service.

Computing device 200 includes a processor 204, main memory 206, ROM 208, an input device 212, an output device such as a display 214, a communication interface 216, among other components including, for example, a receiver and a transceiver. Computing device 200 may also be provided with a storage device 210, such as a microdrive or other device, to provide additional storage. Each of the components are interconnected using various buses, and several of the components may be mounted on a common motherboard or in other manners as appropriate.

Computing device 200 may communicate wirelessly through communication interface 216, which may include digital signal processing circuitry where necessary. Communication interface 216 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver. In addition, short-range communication may occur, such as using a Bluetooth, WiFi, or other such transceiver (not shown). In addition, a GPS (Global Positioning system) receiver module may provide additional navigation- and location-related wireless data to computing device 200, which may be used as appropriate by applications running on computing device 200.

Figure 3:
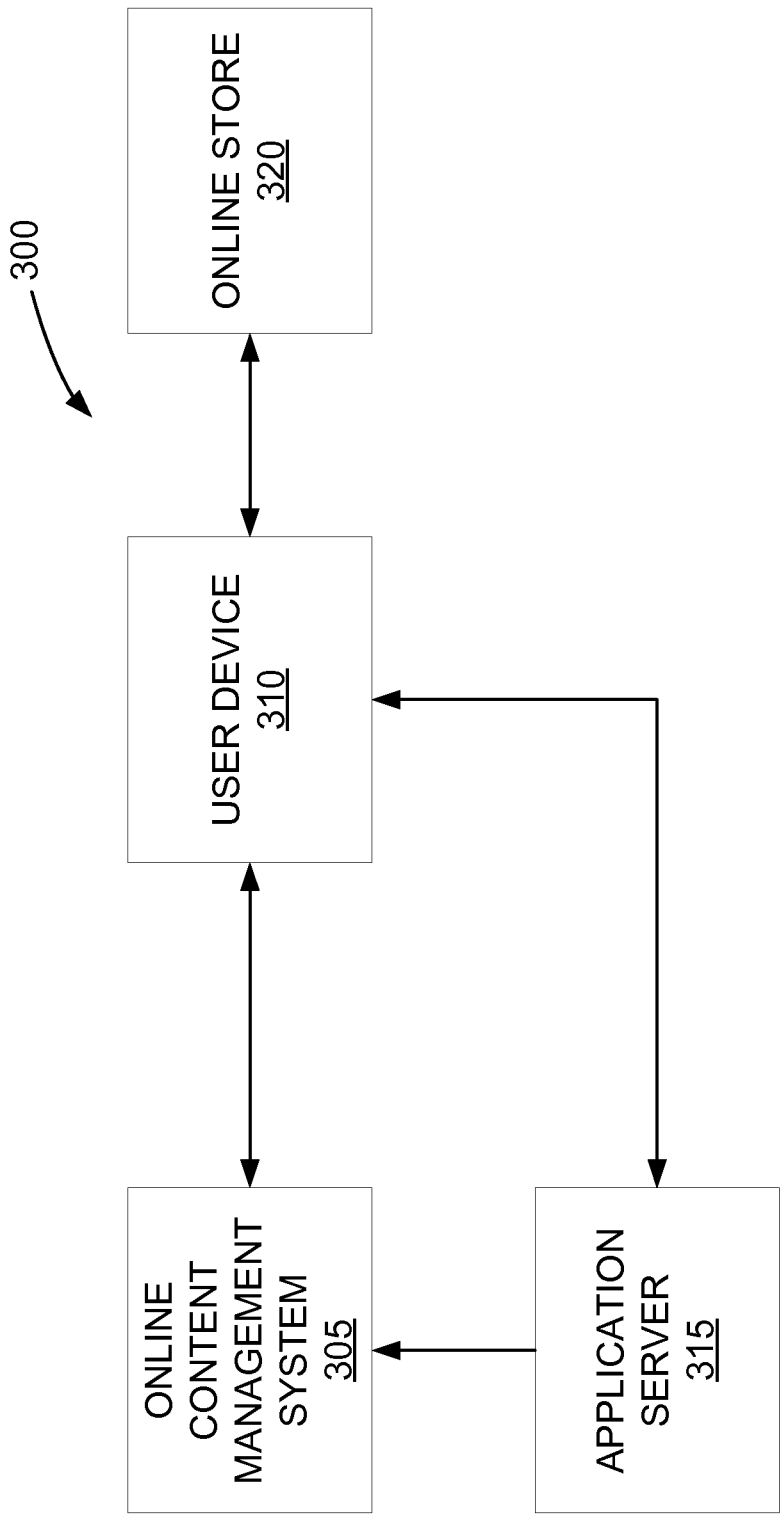
FIG. 3 is a simplified dataflow diagram showing a dataflow for transferring a state of user interaction with an online content item to a computer program associated with the online content item and accessible by a user computer device using the network environment shown in FIG. 1.

FIG. 3 is a simplified dataflow diagram showing a dataflow 300 for transferring a state of user interaction with an online content item to a computer program associated with the online content item and accessible by a user computer device using the network environment shown in FIG. 1. In the example embodiment, an online content management server 305 (OCMS) (e.g., Double-click for Publisher) (also known as an online content management computer device), such as CMS 106 shown in FIG. 1, serves an interactive online content item (e.g., interactive advertisement) to a user device 310 (also known as a client computing device), such as user access device 108 shown in FIG. 1. In some embodiments, OCMS 305 is also known as an ad server. In the example embodiment, the interactive online content item is an advertisement for a computer program or application (e.g., a game or messaging app) that allows the user of user device 310 to interact directly with the advertisement. In some embodiments, the interactive online content item is a simulation of the computer program, in other embodiments the interactive online content item is the actual computer program. For example, the interactive online content item may be an advertisement for a game and allow the user to play the first couple levels of the game. In other examples, the interactive online content item may be for a messaging program or a grocery list generator that allow the user to try the program.

In the example embodiment, OCMS 305 associates the interactive online content item to an interactive session of the computer program, which is hosted on an application server 315 (also known as an application server computing device), such as content provider 102 shown in FIG. 1. In the example embodiment, the application server hosts a plurality of instances of the computer program, and stores the user interactions with each instance of the computer program. In some embodiments, application server 315 is associated with the creator of the computer program (i.e., the developer). In other embodiments, application server 315 is associated with the advertiser of the computer program (i.e., the advertising or marketing company). In still other embodiments, application server 315 is associated with the seller of the computer program (i.e., the computer game store).

When OCMS 305 serves the interactive online content item to user device 310, OCMS 305 also includes a session token with the online content item to identify which interactive session is connected to that interactive online content item. In the example embodiment, OCMS 305 retrieves the session token from application server 315 prior to serving the interactive online content item to user device 310. In the example embodiment, the interactive online content item directly communicates with application server 315. For example, every interaction that the user makes is transmitted from user device 310 to the session on application server 315 associated with that interactive online content item. Application server 315 hosts the computer program, stores the interactions received from the user, and determines the response that the computer program makes. Application server 315 transmits the response back to be displayed on user device 310. In other embodiments, the interactive online content item is in indirect communication with application server 315. For example, the interactive online content item simulates the computer program by receiving user interactions and displaying responses. At periodic intervals (i.e., when a level of the game is completed), the interactive online content item transmits the current state of user interaction (i.e., score, level, and bonuses earned) (also known as session state) and the session token from user device 310 to application server 315. Application server 315 stores the current state of user interaction and associates it with the session token.

In some other embodiments, the interactive online content item communicates with application server 315 through OCMS 305. These communications include the session token to identify which session on application server 315 the communications are associated with. In some embodiments, OCMS 305 is aware of the user's account information (i.e., the user is logged in while interacting with the interactive online content item). In these embodiments, OCMS 305 associates the user's identity with the session token. The user of user device 310 then interacts with the interactive online content item, for example playing the first two levels of the game. Application server 315 stores the state of interaction between the interactive online content item and the user. In the game example, the state of interaction could include the score, level, and any bonuses or awards that the user has earned. For the messaging program, the state of interaction may include any messages sent, messages received, and any contacts in the program.

When the user decides to acquire or install the computer program on the user device, the interactive online content item provides a virtual button or other selectable object to direct the user to a portion of an online store hosted on an online store server 320 where the user may acquire or download the computer program. The online store could also be an application store on a mobile device, a website, or other online location to acquire the computer program. In the example embodiment, OCMS 305 transmits the session token to online store server 320, which online store server 320 associates with the computer program. In other embodiments, OCMS 305 may transfer the session token and the user identity to online store server 320. In some embodiments, the user provides an identity to online store server 320, which associates that identity with the session token.

In some embodiments, online store server 320 embeds the user token in the computer program. After the user downloads or accesses the computer program, the computer program communicates the session token to application server 315 to retrieve the state of user interaction. In other embodiments, online store server 320 communicates the session token directly to application server 315 via an application programming interface (API) and receives the state of user interaction. In yet another embodiment, online store server 320 may provide an API, which allows application server 315 to transmit a user identity to online store server 320. Online store server 320 responds with all session tokens related to that user identity for all computer programs that the application server is responsible for. The API would also indicate which computer program is associated with each session token.

In the example embodiment, once the user has acquired the computer program from online store server 320, the computer program uses the session token to retrieve the state of interaction from application server 315. The computer program then changes at least one attribute of the computer program based on the state of interaction. For example, if the user had completed the first two levels of a game, then the computer program would allow the user to keep his or her score from the interactive online content item and play the third level of the game. In another example, if the program was a messaging program, then the computer program would be updated with any messages that the user had sent or received while using the interactive online content item.

In some embodiment, the user acquires an account for the computer program, where the computer program is executed on application server 315. Online store server 320 associated the session token with the account for the computer program. Upon activation of the account, application server 315 updates the account based on the state of user interaction.

In some embodiments, the user may actually already own the computer program. By interacting with the interactive online content item and then opening the computer program, the user might earn a bonus for returning to the computer program. In these embodiments, the session token is transmitted directly or indirectly to the computer program. Then the computer program may retrieve the state of user interaction from application server 315.

Figure 4:
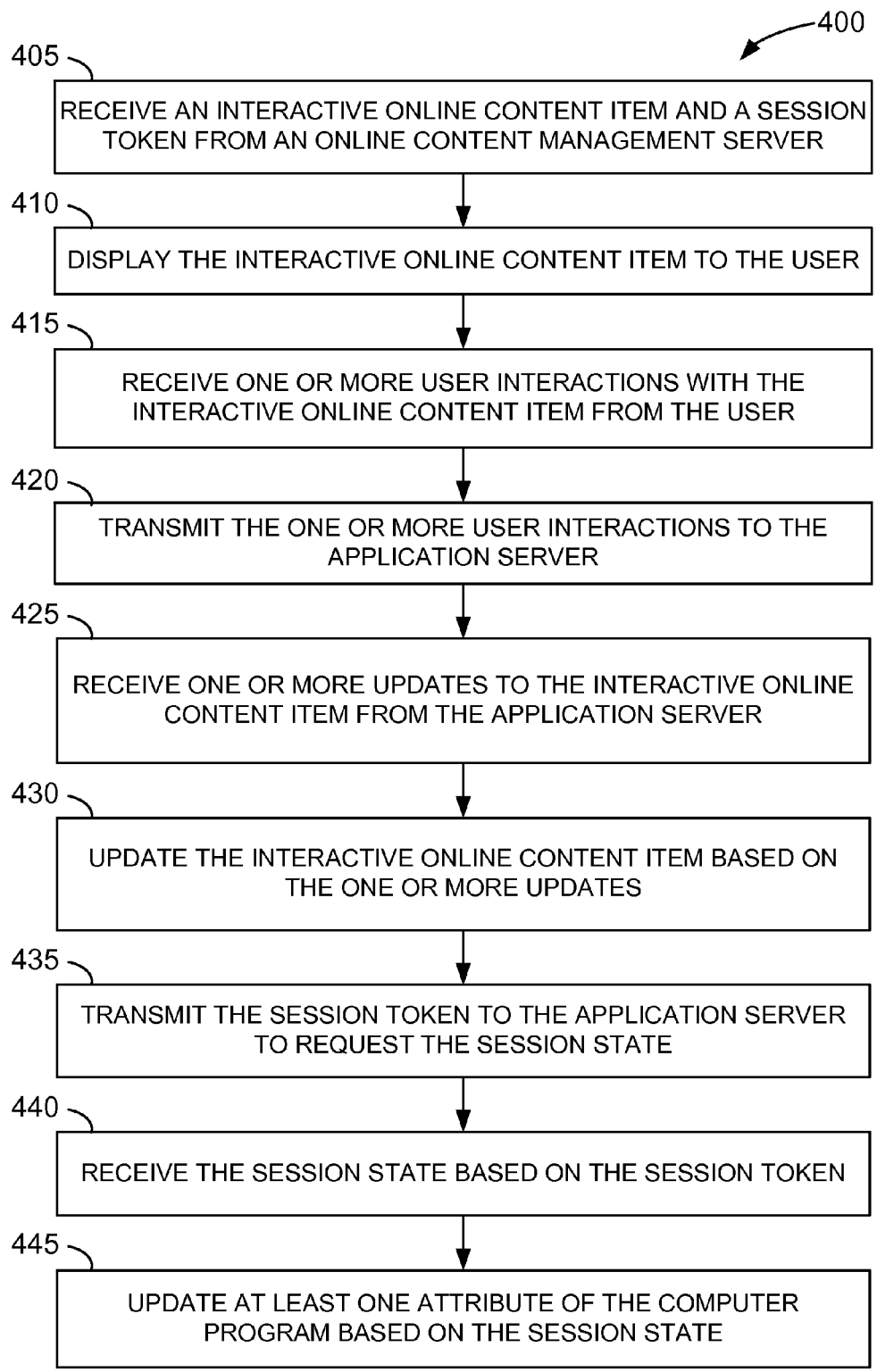
FIG. 4 is a flowchart of an example process for transferring a state of user interaction with an online content item to a computer program associated with the online content item.

FIG. 4 is a flowchart of an example process 400 for transferring a state of user interaction with an online content item to a computer program associated with the online content item. User device 310 (shown in FIG. 3) receives 405 an interactive online content item and a session token for that interactive online content item from OCMS 305 (shown in FIG. 3). User device 310 displays 410 the interactive online content item to the user, such as through display 214 (shown in FIG. 2). User device 310 receives 415 one or more user interactions with the interactive online content item from the user, such as through input device 212 (shown in FIG. 2). User device 310 transmits 420 the one or more user interactions to application server 315 (shown in FIG. 3). In some embodiments, application server 315 receives the session token from user device 310 along with the one or more user interactions. In other embodiments, the interactive online content item executes on application server 315, which is in constant communication with user access device. Application server 315 updates the session associated with the interactive online content item corresponding to the interactive online content item on user device 310 and stores a session state to represent the current state of the interactions between the user and the interactive online content item.

User device 310 receives 425 one or more updates to the interactive online content item from application server 315. User device 310 updates 430 the interactive online content item based on the one or more updates. User device 310 transmits 435 the session token to application server 315 to request the session state. In the example embodiment, user device 310 requests the session state after the user has acquired the computer program. User device 310 receives 440 the session state from application server 315. User device 310 updates 445 at least one attribute of the computer program based on the session state.

FIG. 5 is a diagram 500 of a plurality of components of one or more example computing devices 200, included in the environment shown in FIG. 1. For example, one or more of computing devices 200 may be user access devices 108, shown in FIG. 1, or may be user device 310, shown in FIG. 3. FIG. 5 further shows a configuration of a database 530 contained within user device 310.

User device 310 includes receiving component 502 for receiving an interactive online content item and session token, as describe with reference to step 405 (FIG. 4). User device 310 also includes a display component 504 for displaying the interactive online content item to the user, as described with reference to step 410 (FIG. 4). User device 310 further includes a receiving component 506 to receive one or more user interactions with the interactive online content item from the user, as described with reference to step 415 (FIG. 4). Moreover, user device 310 includes a transmitting component 508 for transmitting the one or more user interactions to the application server 315 (shown in FIG. 3), as described with reference to step 420 (FIG. 4). In addition, user device 310 includes a receiving component 510 to receive one or more updates to the interactive online content item from application server 305, as described with reference to step 425 (FIG. 4). User device 310 also includes an updating component 512 for updating the interactive online content item based on the one or more updates, as described with reference to step 430 (FIG. 4). User device 310 further includes a transmitting component 514 for transmitting the session token to application server 315 to request the session state, as described with reference to step 435 (FIG. 4). Moreover, user device 310 includes a receiving component 516 to receive the session state based on the session token from application server 315, as described with reference to step 440 (FIG. 4). In addition, user device 310 includes an updating component 518 for updating at least one attribute of the computer program based on the session state, as described with reference to step 445 (FIG. 4).

In an example embodiment, the database 530 is divided into a plurality of sections, including but not limited to, an interactive online content items section 520 which may include received interactive online content items, a session tokens 522 which may include session tokens for received interactive online content items, a computer programs section 524 which may include acquired computer programs, and a user account information section 526. These sections within database 530 are interconnected to perform the functions described above.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

It will be appreciated that the above embodiments that have been described in particular detail are merely example or possible embodiments, and that there are many other combinations, additions, or variations that may be included.

Also, the particular naming of the components, capitalization of terms, the attributes, data structures, or any other programming or structural aspect is not mandatory or significant, and the mechanisms that implement the subject matter described herein or its features may have different names, formats, or protocols. Further, the system may be implemented via a combination of hardware and software, as described, or entirely in hardware elements. Also, the particular division of functionality between the various system components described herein is merely for the purposes of example only, and not mandatory; functions performed by a single system component may instead be performed by multiple components, and functions performed by multiple components may instead performed by a single component.

Some portions of above description may present features in terms of algorithms and symbolic representations of operations on information. Such algorithmic descriptions and representations may be used by those skilled in the data processing arts to most effectively convey the substance of their work to others skilled in the art. These operations, while described functionally or logically, are understood to be implemented by computer programs. Furthermore, it has also proven convenient at times, to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or "providing" or the like, refer to the action and processes of a computer system, or similar electronic computing device, that manipulates and transforms data represented as physical (electronic) quantities within the computer system memories or registers or other such information storage, transmission or display devices.

Based on the foregoing specification, the above-discussed embodiments may be implemented using computer programming or engineering techniques including computer software, firmware, hardware or any combination or subset thereof. Any such resulting program, having computer-readable and/or computer-executable instructions, may be embodied or provided within one or more computer-readable media, thereby making a computer program product, i.e., an article of manufacture. The computer readable media may be, for instance, a fixed (hard) drive, diskette, optical disk, magnetic tape, semiconductor memory such as read-only memory (ROM) or flash memory, etc., or any transmitting/receiving medium such as the Internet or other communication network or link. The article of manufacture containing the computer code may be made and/or used by executing the instructions directly from one medium, by copying the code from one medium to another medium, or by transmitting the code over a network.

While the disclosure has been described in terms of various specific embodiments, it will be recognized that the disclosure can be practiced with modification within the spirit and scope of the claims.

What is claimed is:

1. A computer-based method for transferring user interactions with an online content item to a computer program accessible by a user device, said method implemented using an application server in communication with a memory, said method comprising:
hosting, on the application server, a plurality of remote interaction sessions with an interactive online content item associated with a computer program, wherein each remote interaction session includes a session state;
receiving, by the application server, a first token to be associated with a remote interaction session;
determining a first remote interaction session, from the plurality of remote interaction sessions, not previously associated with any token;
associating, by the application server, the first token with the first remote interaction session, wherein the first token uniquely identifies the first remote interaction session;
receiving, from a user device, one or more remote user interactions with the interactive online content item;
updating the session state for the first remote interaction session based on the one or more user interactions;
receiving, from the user device, a request for the session state for the first remote interaction session after the computer program becomes accessible for local use by the user device, wherein the request for the session state includes the first token;
retrieving, by the application server, the session state for the first remote interaction session responsive to receipt of the first token in the request; and
transmitting, to the user device, the session state for the first session to be applied to local execution of the computer program.

2. The method of claim 1, further comprising:
generating the first token; and
transmitting, to an online content management system, the first token and the interactive online content item, wherein the interactive online content item is to be displayed on the user device and allow the user to interact with the computer program.

3. The method of claim 1, wherein updating the session state for the first remote interaction session further comprises:
determining one or more responses to the one or more user interactions, wherein the one or more responses are generated from inputting the one or more user interactions into the computer program;
transmitting, to the user device, the one or more responses for display on the user device within the interactive online content item; and
updating the session state based on the one or more responses.

4. The method of claim 1, wherein each remote interaction session of the plurality of remote interaction sessions includes a simulation of the computer program being executed.

5. The method of claim 1, wherein the first remote interaction session is configured to enable the user device to interact with the computer program through the interactive online content item.

6. The method of claim 1, further comprising:
hosting, on the application server, the computer program, wherein the computer program is accessible via a user account;
receiving user account information to access the user account;
transmitting, to an online store server, a request for tokens, wherein the request for tokens includes the user account information;
receiving, from the online store server, one or more tokens associated with the user account information;
retrieving the session state for each remote interaction session associated with each of the one or more tokens; and
updating at least one attribute of the user account based on at least one of the retrieved session states.

7. The method of claim 1, wherein the request for the session state for the first remote interaction session is received from an online store server, and the session state for the first remote interaction session is transmitted to the online store server to be included with the computer program when the user device downloads the computer program for local execution.

8. The method of claim 1, wherein the interactive online content item includes a link to acquire the computer program, and wherein the link directs the user device to an online store server where the user device may acquire the computer program for local execution.

9. An application server for transferring a state of user interaction with an online content item to a computer program accessible by a user device, said application server includes at least one processor communicatively coupled to at least one memory device, said application server is configured to:
host a plurality of remote interaction sessions with an interactive online content item associated with a computer program, wherein each remote interaction session includes a session state;
receive a first token to be associated with a remote interaction session;
determine a first remote interaction session, from the plurality of remote interaction sessions, not previously associated with any token;
associate the first token with the first remote interaction session, wherein the first token uniquely identifies the first remote interaction session;
receive one or more remote user interactions with the interactive online content item from a user device;
update the session state for the first remote interaction session based on the one or more user interactions;
receive a request for the remote interaction session state for the first session from the user device after the computer program becomes accessible for local use by the user device, wherein the request for the session state includes the first token;

retrieve the session state for the first remote interaction session responsive to receipt of the first token in the request; and transmit the session state for the first session to the user device to be applied to local execution of the computer program.

10. The application server in accordance with claim 9, wherein the application server is further configured to:
generate the first token; and
transmit the first token and the interactive online content item to an online content management system, wherein the interactive online content item is to be displayed on the user device and allow a user to interact with the computer program.

11. The application server in accordance with claim 9, wherein the application server is further configured to:
determine one or more responses to the one or more user interactions, wherein the one or more responses are generated from inputting the one or more user interactions into the computer program;
transmit the one or more responses for display on the user device within the interactive online content item; and
update the session state based on the one or more responses.

12. The application server in accordance with claim 9, wherein each remote interaction session of the plurality of remote interaction sessions includes a simulation of the computer program being executed.

13. The application server in accordance with claim 9, wherein the first remote interaction session is configured to enable the user device to interact with the computer program through the interactive online content item.

14. The application server in accordance with claim 9, wherein the application server is further configured to:
host the computer program, wherein the computer program is accessible via a user account;
receive user account information to access the user account;
transmit a request for tokens to an online store server, wherein the request for tokens includes the user account information;
receiving one or more tokens associated with the user account information from the online store server;
retrieve the session state for each remote interaction session associated with each of the one or more tokens; and
update at least one attribute of the user account based on at least one of the retrieved session states.

15. The application server in accordance with claim 9, wherein the request for the session state for the first remote interaction session is received from an online store server, and the session state for the first remote interaction session is transmitted to the online store server to be included with the computer program when the user device downloads the computer program.

16. The application server in accordance with claim 9, wherein the interactive online content item includes a link to acquire the computer program, and wherein the link directs the user device to an online store server where the user device may acquire the computer program for local execution.

17. A non-transitory computer-readable storage device having processor-executable instructions embodied thereon, for transferring a state of user interaction with an online content item to a computer program accessible by a user device, wherein when executed by an application server communicatively coupled to a memory, the processor executable instructions cause the application server to:
host a plurality of remote interaction sessions with an interactive online content item associated with a computer program, wherein each remote interaction session includes a session state;
receive a first token to be associated with a remote interaction session;
determine a first remote interaction session, from the plurality of remote interaction sessions, not previously associated with any token;
associate the first token with the first remote interaction session, wherein the first token uniquely identifies the first remote interaction session;
receive one or more remote user interactions with the interactive online content item from a user device;
update the session state for the first remote interaction session based on the one or more user interactions;
receive a request for the remote interaction session state for the first session from the user device after the computer program becomes accessible for local use by the user device, wherein the request for the session state includes the first token;
retrieve the session state for the first remote interaction session responsive to receipt of the first token in the request; and
transmit the session state for the first session to the user device to be applied to local execution of the computer program.

18. An online content management system for transferring a state of user interaction with an online content item to a computer program accessible for local use by a user device, said online content management system includes at least one processor communicatively coupled to at least one memory device, said online content management system is in communication with a user device and an application server, said online content management system is configured to:
receive a first token for one of a plurality of remote interaction sessions with an interactive online content item associated with a computer program from the application server;
determine a first remote interaction session, from the plurality of remote interaction sessions, not previously associated with any token;
associate the first token with the first remote interaction session;
transmit the first token and an interactive online content item to a user device, wherein the first token uniquely identifies the first remote interaction session, and wherein the user device is instructed to display the interactive online content item to a user;
receive one or more remote user interactions with the interactive online content item and the first token from the user device;
transmit the one or more remote user interactions and the first token to the application server, wherein the application server updates a session state for the first remote interaction session based on the one or more user interactions;
receive user account information from the user device;
associate the first token with the user account information;
receive a user selection to acquire the computer program; and
transmit the user account information and first token to the online store server, wherein the online store server is configured to deliver the computer program and first token to the user device;

receive from the user device, a request for the session state for the first remote interaction session after the computer program becomes accessible for local use by the user device, wherein the request for the session state includes the first token;

retrieve the session state for the first remote interaction session responsive to receipt of the first token in the request; and transmit the session state for the first session to be applied to local execution of the computer program.

* * * * *